(12) United States Patent
Williams et al.

(10) Patent No.: US 8,886,340 B2
(45) Date of Patent: *Nov. 11, 2014

(54) METHOD AND APPARATUS FOR RETAINING MEDICAL IMPLANTS WITHIN BODY VESSELS

(75) Inventors: Michael S. Williams, Santa Rosa, CA (US); Terrance Ransbury, Chapel Hill, NC (US); Richard A. Glenn, Santa Rosa, CA (US); Kevin Holbrook, Chapel Hill, NC (US)

(73) Assignee: Interventional Autonomics Corporation, Chapel Hill, NC (US)

( * ) Notice: Subject to any disclaimer, the term of this patent is extended or adjusted under 35 U.S.C. 154(b) by 165 days.

This patent is subject to a terminal disclaimer.

(21) Appl. No.: 12/908,086

(22) Filed: Oct. 20, 2010

(65) Prior Publication Data

US 2011/0054555 A1    Mar. 3, 2011

Related U.S. Application Data

(63) Continuation of application No. 12/506,232, filed on Jul. 20, 2009, now Pat. No. 7,840,282, which is a continuation of application No. 10/977,060, filed on Oct. 29, 2004, now Pat. No. 7,617,007, which is a continuation-in-part of application No. 10/454,223, filed on Jun. 4, 2003, now Pat. No. 7,082,336, and a continuation-in-part of application No. 10/453,971, filed on Jun. 4, 2003, now Pat. No. 8,239,045, and a continuation-in-part of application No. 10/862,113, filed on Jun. 4, 2004, now Pat. No. 7,529,589.

(60) Provisional application No. 60/515,746, filed on Oct. 30, 2003, provisional application No. 60/543,260, filed on Feb. 10, 2004.

(51) Int. Cl.
*A61N 1/02* (2006.01)

(52) U.S. Cl.
USPC .............................................. 607/126; 607/2

(58) Field of Classification Search
USPC ..................... 607/2, 5, 9, 14, 115, 116, 126
See application file for complete search history.

(56) References Cited

U.S. PATENT DOCUMENTS

| 5,954,761 A * | 9/1999 | Machek et al. ............... 607/126 |
| 6,442,413 B1 * | 8/2002 | Silver ............................ 600/345 |
| 6,519,488 B2 * | 2/2003 | KenKnight et al. ........... 600/372 |

* cited by examiner

*Primary Examiner* — Brian T Gedeon

(57) ABSTRACT

The present application describes a retention device for anchoring a medical device within the vasculature. The device may include expandable member coupled to an intravascular medical device and proportioned for receipt within a vessel. At least a portion of the expandable member is expandable to radially engage a vessel wall and to thereby retain the medical device within the vessel. The system is suitable for a variety of intravascular devices, including but not limited to ICD's, pacemakers, and intravascular drug delivery systems.

3 Claims, 18 Drawing Sheets

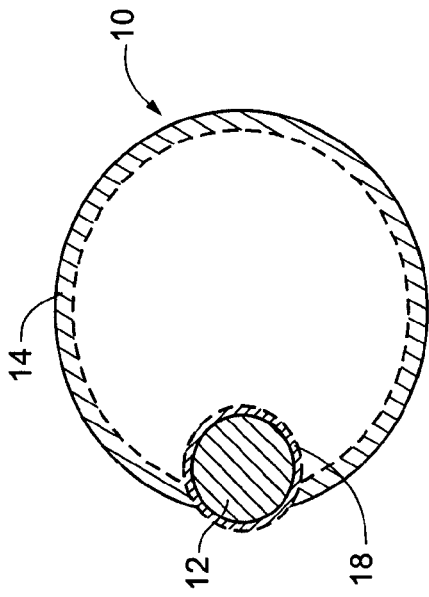
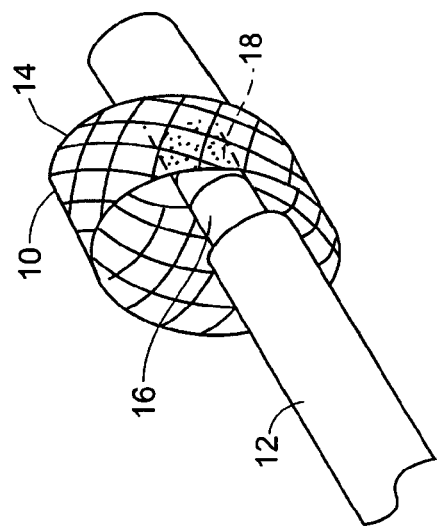

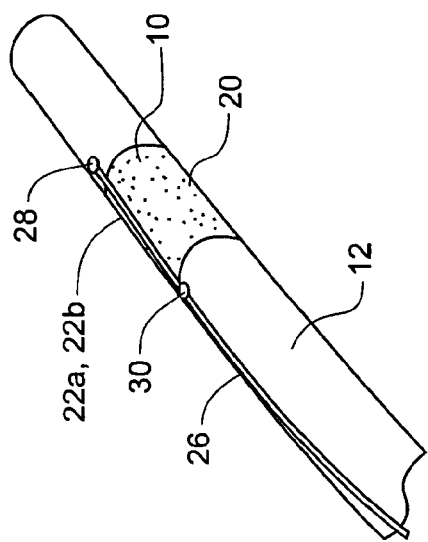

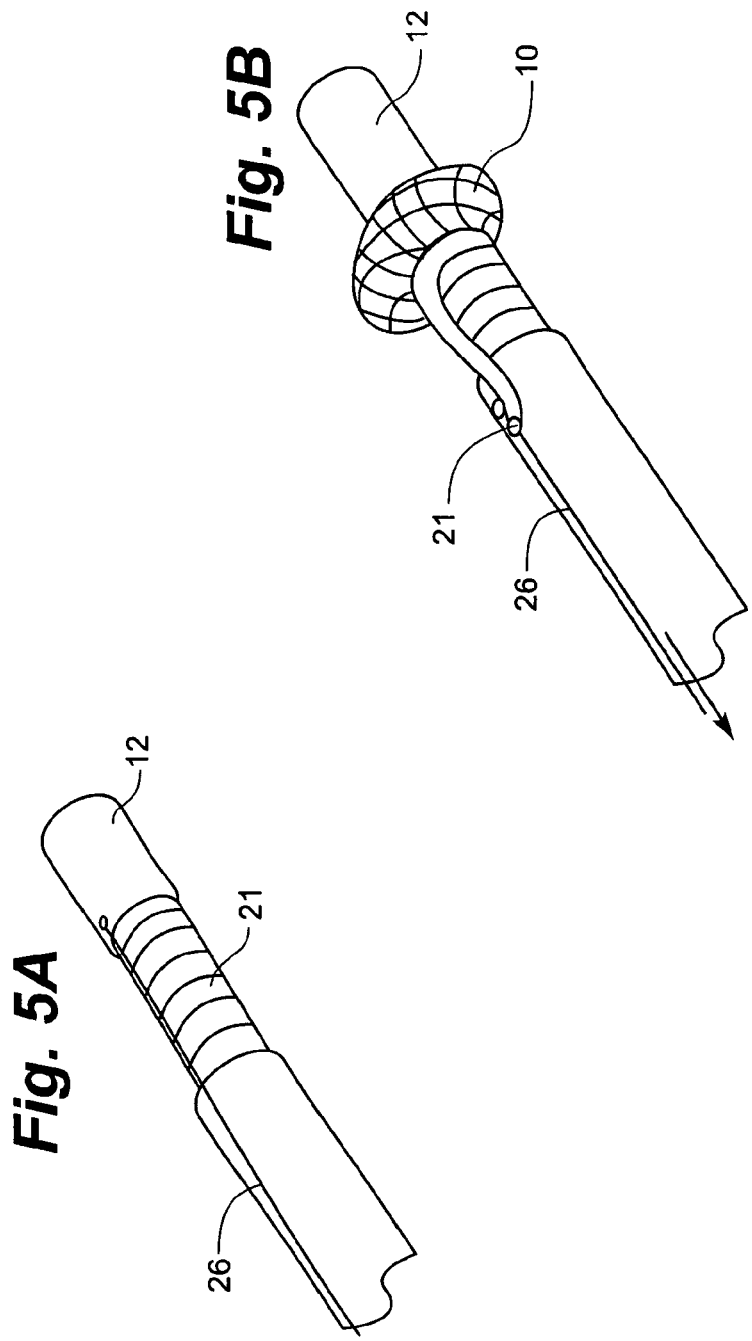

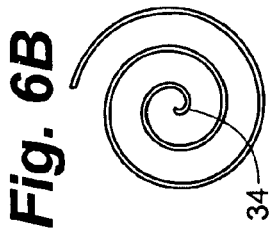
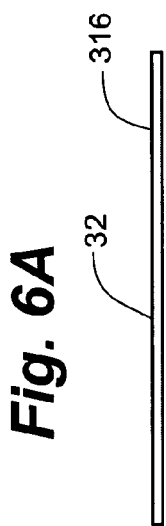
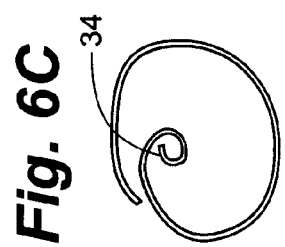

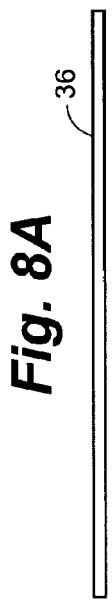
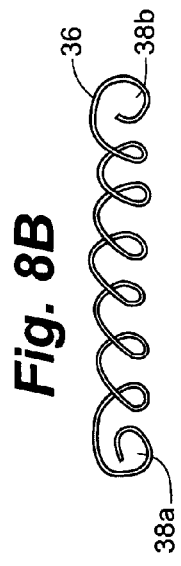
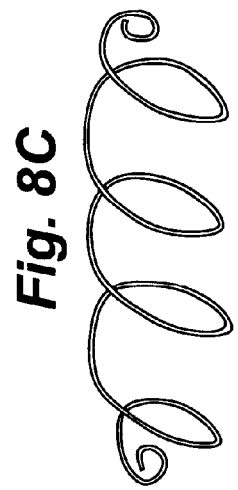
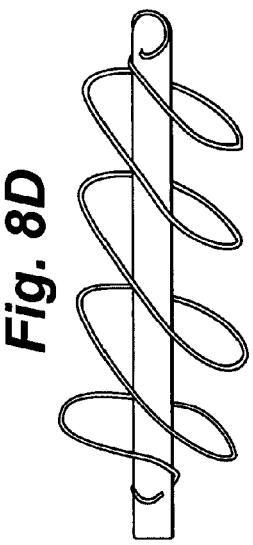
Fig. 8A
Fig. 8B
Fig. 8C
Fig. 8D

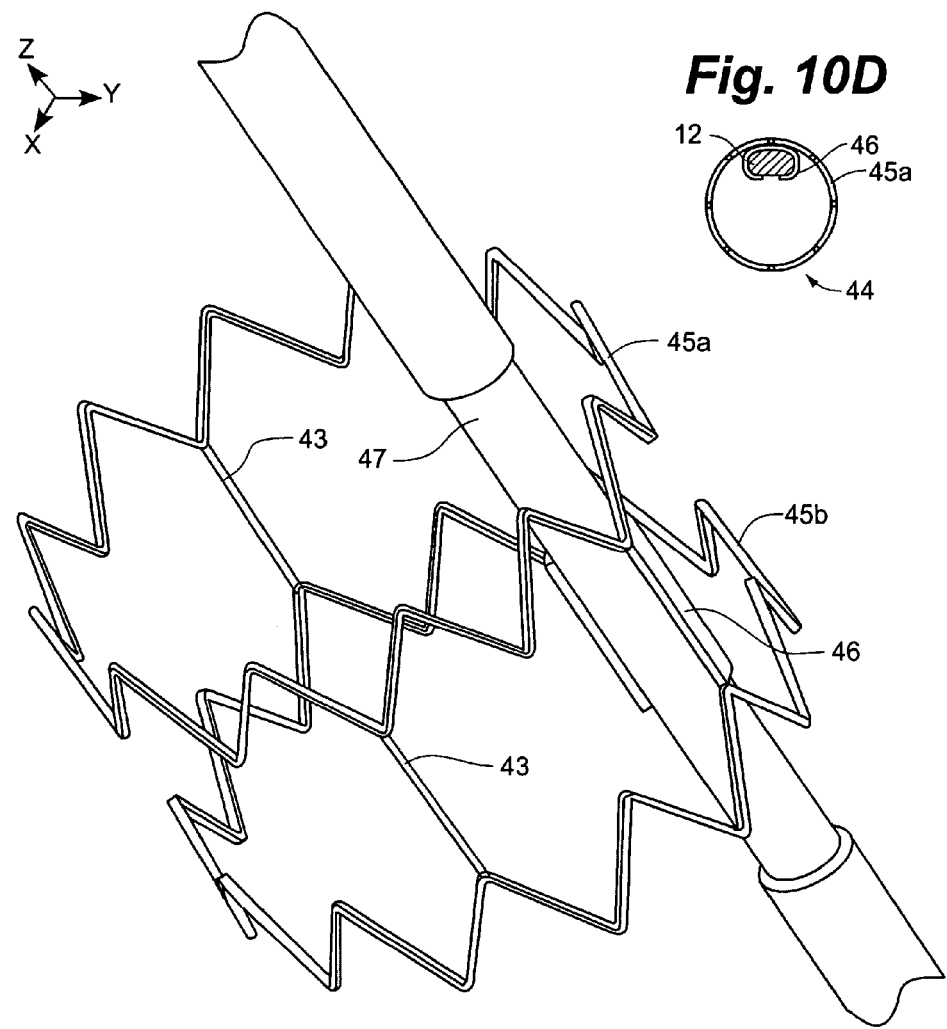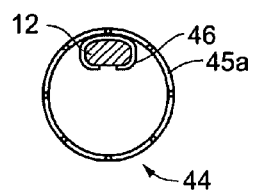

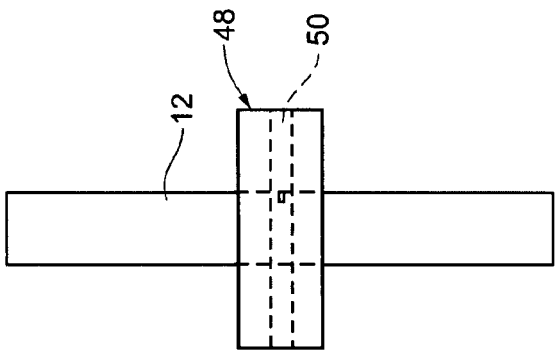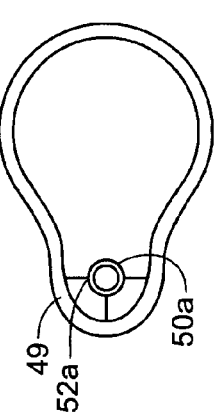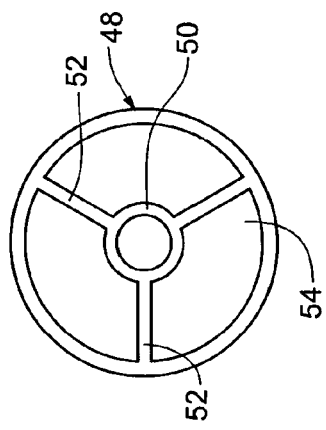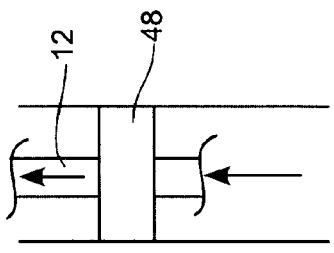

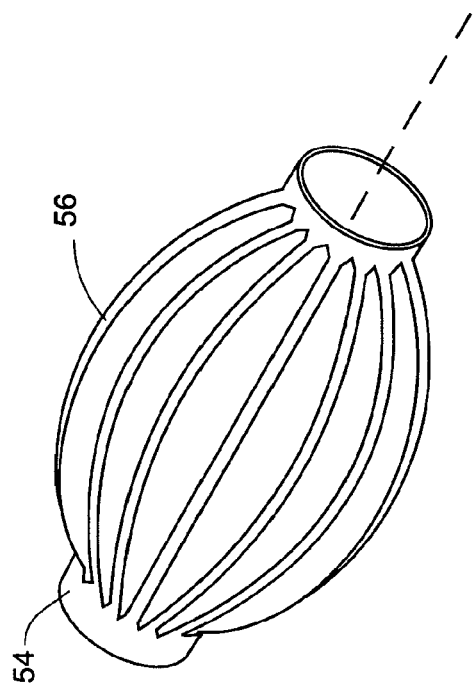
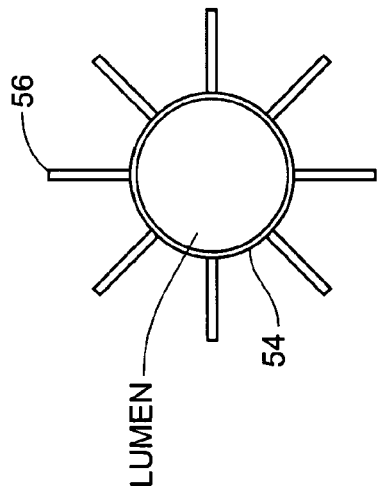

METHOD AND APPARATUS FOR RETAINING MEDICAL IMPLANTS WITHIN BODY VESSELS

PRIORITY

This is a continuation of U.S. application Ser. No. 12/506,232, now U.S. Pat. No. 7,840,282, filed Jul. 20, 2009, which is a continuation of U.S. application Ser. No. 10/977,060, now U.S. Pat. No. 7,617,007, filed Oct. 29, 2004, which is a continuation-in-part of U.S. application Ser. No. 10/454,223, now U.S. Pat. No. 7,082,336, filed Jun. 4, 2003, U.S. application Ser. No. 10/453,971, filed Jun. 4, 2003, and U.S. application Ser. No. 10/862,113, now U.S. Pat. No. 7,529,289, filed Jun. 4, 2004, and claims the benefit of U.S. Provisional Application No. 60/515,746, filed Oct. 30, 2003 and U.S. Provisional Application No. 60/543,260, filed Feb. 10, 2004.

FIELD OF THE INVENTION

The present invention generally relates to devices, systems, and methods for retaining medical implants within the body. In particular, the invention provides methods and systems for implanting and retaining medical devices within a patient's vasculature.

BACKGROUND OF THE INVENTION

Pacemakers, defibrillators and implanted cardioverter defibrillators ("ICDs") have been successfully implanted for years for treatment of heart rhythm conditions.

Pacemakers are implanted in patients who have bradycardia (slow heart rate). The pacemakers detect periods of bradycardia and deliver electrical stimuli to increase the heartbeat to an appropriate rate.

ICDs are implanted in patients who may suffer from episodes of fast and irregular heart rhythms called tachyarrhythmias. An ICD can cardiovert the heart by delivering electrical current directly to the heart to terminate an atrial or ventricular tachyarrhythmia, other than ventricular fibrillation. An ICD may alternatively defibrillate the heart in a patient who may stiffer ventricular fibrillation (VF), a fast and irregular heart rhythm in the ventricles. During a VF episode, the heart quivers and can pump little or no blood to the body, potentially causing sudden death. An ICD implanted for correction of ventricular fibrillation will detect a VF episode and deliver an electrical shock to the heart to restore the heart's electrical coordination.

Another type of implantable defibrillation device treats patients who may suffer from atrial fibrillation (AF), which is a loss of electrical coordination in the heart's upper chambers (atria). During AF, blood in the atria may pool and clot, placing the patient at risk for stroke. An electrophysiological device implanted for correction of atrial fibrillation will detect an AF episode and deliver an electrical shock to the atria to restore electrical coordination.

Pacemakers and ICDs are routinely implanted in the pectoral region either under the skin (subcutaneous) or under the pectoral muscle. The leads are placed at appropriate locations within or on the heart. Because of this complexity, a cardiologist identifying a heart rhythm condition may be required to refer his or her patient to sub-specialists or surgeons for implantation of a pacemaker or ICD—thus delaying implantation of the device in a patient who urgently needs it. It is thus desirable to simplify these devices and the procedures for implanting them so as to permit their implantation by a broader range of physicians.

U.S. application Ser. No. 10/453,971, filed Jun. 4, 2003, and Ser. No. 10/862,113, filed Jun. 4, 2004, describe intravascular systems that may be used to deliver electrical energy to the heart such as for defibrillation, pacing, and/or cardioversion of the heart. These applications are incorporated herein by reference for all purposes.

Generally speaking, the systems described in the '971 and '113 applications include at least one housing containing the necessary circuitry and related components, and optionally include at least one lead carrying the electrodes needed to deliver the electrical energy to the body. Some or all of these components are positioned within the vasculature, such as in the superior vena cava ("SVC"), the inferior vena cava ("IVC"), the left or right subclavian vein ("LSV" or "RSV"), coronary sinus and/or within other vessels in the venous or arterial system. For some of the implant components (such as the housing and/or lead), retention devices are needed to retain the implant within the vasculature.

The '971 and '113 applications sleeves or anchors that may be introduced after the implant to be retained has been positioned at a desired location within the vessel, or that may be introduced simultaneously with the implant. In some embodiments, the anchor is positioned adjacent the implant and expanded to a radially expanded position. During this expansion step the retention sleeve may self-expand and/or it may be expanded using an expansion tool such as a balloon passed into the retention sleeve's central lumen and subsequently inflated. When the retention sleeve is expanded, its radial forces engage the implant and secure the implant against the vessel wall. Blood flowing through the vessel passes through the tubular interior of the retention sleeve.

The '971 and '113 applications describe the retention devices as being either separate components from the implants they are intended to retain, or as being integral with the retained components. The present application is directed to alternative retention devices for supporting medical implants within blood vessels. Although the focus of this description is on retention devices that are integrated with the medical implants they retain, they are equally useful as components that are physically separate or separable from the medical implants. It should also be noted that although these retention devices will be described in the context of intravascular cardioverters, defibrillators, and or pacemakers, they are equally suitable for any type of medical implant that must be retained within a blood vessel.

SUMMARY

The following presents a simplified summary of the invention in order to provide a basic understanding of some of its aspects. This summary is not an extensive overview of the invention and is intended neither to identify key or critical elements of the invention nor to delineate its scope. The primary purpose of this summary is to present some concepts of the invention in a simplified form as a prelude to the more detailed description that is presented later.

The present application describes an expandable member coupled to an intravascular medical device and proportioned for receipt within a vessel. At least a portion of the expandable member is expandable to radially engage a vessel wall and to thereby retain the medical device within the vessel.

BRIEF DESCRIPTION OF THE DRAWINGS

FIG. 1A is perspective view of a medical implant and a retention device for retaining the medical implant within a body vessel. The retention device is shown in the expanded position.

FIG. 1B is a cross-sectional end view of the retention device and medical implant of FIG. 1A, with the retention device in the expanded position.

FIG. 2A is a perspective view similar to FIG. 1A, showing the retention device in the contracted position and covered by a removable sheath.

FIG. 2B is a cross-sectional top view of the retention device and medical implant as shown in FIG. 2A, however for clarity the sheath is not shown.

FIG. 5A is a perspective view similar to FIG. 2A showing an alternative sheath configuration.

FIG. 5B is a perspective view similar to FIG. 5A showing removal of the sheath to release the retention device.

FIG. 6A is a side elevation view showing one configuration of a retention device in a flattened position.

FIGS. 6B and 6C are top plan views showing the retention device of FIG. 6A in rolled positions. In FIG. 6B, the retention device is rolled into a streamlined position for passage through a vessel; in FIG. 6C the retention device is expanded from the FIG. 6B position for retaining an attached medical implant within a vessel.

FIG. 8A is a side elevation view showing one configuration of a retention device in a flattened position.

FIGS. 8B and 8C are perspective views showing the retention device of FIG. 8A in rolled positions. In FIG. 8B, the retention device is rolled into a streamlined position for passage through a vessel; in FIG. 8C the retention device is expanded from the FIG. 8B position for retaining an attached medical implant within a vessel. FIG. 8D is similar to FIG. 8C but shows the retention device attached to a medical implant.

FIG. 10C is a side elevation view similar to FIG. 10B, showing one of the retention devices in closer detail.

FIG. 10D is a top plan view showing the retention device of FIG. 10C, and showing the medical implant in cross-section.

FIG. 11A is a top plan view of an alternative retention device.

FIG. 11B is a side elevation view of the alternative retention device of FIG. 11A.

FIG. 11C is a side elevation view showing the retention device of FIG. 11A retaining a medical implant within a vessel.

FIG. 11D is a top plan view of a slight modification to the FIG. 11A embodiment, in which the medical implant is offset from the central axis of the retention device.

FIG. 13A is a perspective view of still another embodiment of a retention device.

FIG. 13B is a top plan view of the retention device of FIG. 13A.

DETAILED DESCRIPTION OF THE DRAWINGS

Figure 3A:
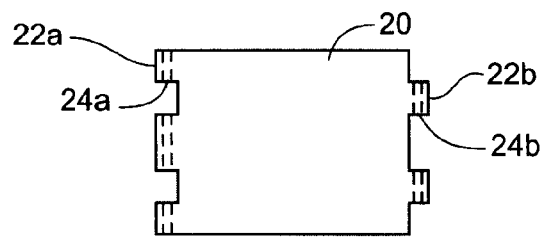
FIG. 3A is a side elevation view showing the removable sheath of FIG. 2A in a flattened position.

FIG. 1A, shows a first embodiment of a retention device or anchor 10 for retaining a medical implant 12 in the patient's vasculature, such as in the superior vena cava, inferior vena cava, or the left or right subclavian. The medical implant 12 may be a portion of an implantable defibrillator, cardioverter and/or pacemaker of the type described in U.S. application Ser. No. 10/453,971. For example, the implant may be a housing containing certain components such as circuitry, electronics, batteries and/or capacitors, or it may be a lead having one or more electrodes for delivering the necessary defibrillation, cardioversion or pacing pulse and/or for sensing the electrical activity of the heart. However, the retention device is not limited to use in the cardiovascular area, and may be equally suitable for retaining other types of implants. Such implants might include, for example, artificial pancreas implants, implants that gather data concerning properties of the patient's blood (e.g., blood glucose, pH, or oxygen levels or biochemical markers indicative of certain disease conditions) and/or that deliver drugs or other therapies into the blood from within a blood vessel. More particularly, fully implantable intravascular systems may be used for administering drugs including hormones, chemotherapeutic agents, pharmaceuticals, synthetic, recombinant or natural biologics, and other agents within the body. Generally speaking, the systems include drug reservoirs and associated components (e.g., batteries, electronics, motors, pumps, circuitry, telemetric components, sensors) that are anchored in the vasculature and programmed to administer drugs into the bloodstream or directly into certain organs or tissues. The systems may deliver drugs directly from the reservoirs or from elongate microtubules that extend from the reservoirs. Such systems are described in U.S. Provisional Application No. 60/543,260, filed Feb. 10, 2004 which is incorporated herein by reference.

Although various means may be used to retain the implant within the vasculature, one example of a retention device is a tubular retention sleeve or anchor 10 shown in FIG. 1A. The anchor 10 includes a tubular body 14 having a retracted or compressed position in which it is streamlined for implantation (see FIGS. 2A and 2B). The body 14 is expandable to an expanded position (FIGS. 1A and 1B) in which it contacts the surrounding vessel walls to retain the implant 12 in place. The surface of the medical implant may include a recessed portion 16 as shown in FIG. 1A such that the anchor 10 is seated within the recessed portion 16 when it is in its retracted position. This allows the exterior surface of the anchor to sit flush with the exterior surface of the implant for smooth passage through the blood vessel during implantation.

Anchor 10 is joined to the implant 12 by a connector 18 which may be a narrow ring or ellipse at least partially encircling the implant 12 as shown, or which may take an alternative form. Connector 18 may be permanently or detachably connected to the anchor 10 and the implant 12 by welding, adhesives, snap-fit, crimping, or other means. It may also be an integral piece of the anchor 10 that is connected to the implant 12, and/or an integral piece of the implant 12 that is connected to the anchor 10.

In the FIG. 1A embodiment, the anchor 10 and implant 12 are shown connected such that the implant 12 is positioned along the interior perimeter of the anchor 10. This configuration allows the medical implant to be positioned along the wall of the vessel (see, for example, FIG. 8), leaving the remainder of the blood vessel free from obstruction. Other configurations that position the medical implant in a more central position within the blood vessel may also be suitable and are discussed below. Central positioning may be advantageous in that it leaves a larger space between the implant and the vessel wall, thereby minimizing tissue growth onto/into the implant.

The anchor 10 is compressible to a streamlined profile (FIG. 2A) to facilitate implantation, and is preferably self-expanding such that it springs controllably to an opened position when unrestrained. However it may alternatively be expandable using an expansion member such as a balloon or other expandable device that is positioned in the central lumen of the anchor and then expanded or manipulated to expand the anchor. The anchor 10 includes structural features that allow the anchor to radially support the implant against a vessel wall. For example, a band, mesh or other framework formed of one or more shape memory (e.g., nickel titanium alloy, nitinol, thermally activated shape-memory material, or shape memory polymer) elements or stainless steel, Elgiloy, or MP35N elements may be used.

The implant 12 is preferably provided with a smooth polymeric barrier that is both anti-proliferative and anti-thrombogenic and that thereby prevents endothelial growth and thrombus formation on the implant. Examples of materials for the polymeric barrier include, but are not limited to ePTFE, or other fluoropolymers, silicone, non-woven nylon, or biomimetic materials.

The anchor 10 may also include a similar smooth polymeric barrier, which may be a coating or which may be formed by layers of barrier material on the interior and exterior surfaces of the framework, thus encapsulating the anchor between barrier materials although it will be appreciated that the framework and barrier may be combined in a variety of ways to prevent thrombus formation and endothelialization on the anchor walls. Such a barrier membrane may further function to hold the anchor 10 and implant 12 together.

As one alternative (or in addition to the polymetric barrier), the anchor material could include surfaces for eluting non-coagulative, anti-platlet (e.g., IIBIIIA glycoprotein receptor blockers), anti-proliferative, and/or anti-inflammatory substances. As yet another alternative, the anchor 10 may include a surface, membrane and/or coating that allows it to be integrated into the vessel wall via tissue ingrowth.

The structural framework of the anchor may extend through the entire length of the anchor, or it may be included in only a portion of the anchor, such as at the proximal and distal end regions, leaving the intermediate region between them without structural reinforcement. Likewise, the anchor itself may be longitudinally shorter (as in FIG. 1A) or longer than the medical implant 12. If a longitudinally shorter anchor is used, either a single anchor may be used, or two or more such anchors may be used in spaced-apart positions. Other configurations for the anchor that utilize some of these concepts are shown and described in connection with FIGS. 6A through 13B.

Figure 3B:
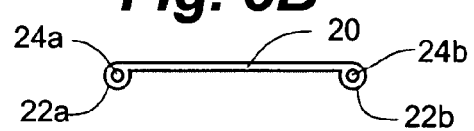
FIG. 3B is a top plan view showing the removable sheath of FIG. 2A in a flattened position.
Figure 3C:
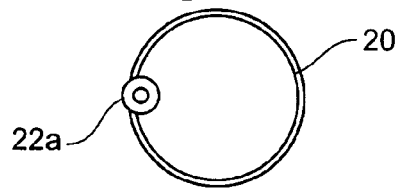
FIG. 3C is a top plan view showing the removable sheath of FIG. 2A in the closed position.

In preparation for implantation, the anchor 10 is compressed to a streamlined positioned for passage through the vasculature. As shown in FIG. 2A, the anchor 10 may be disposed within a removable sheath 20 to facilitate movement through the vasculature. FIGS. 3A-3C show one example of a sheath 20 that may be used for this purpose. Referring to FIG. 3A, sheath 20 may be a thin (e.g., approximately 0.001-0.003 inch) sheet of polymeric material such as FEP, PTFE, etc. If desired, the sheath may alternatively be formed of a bioabsorbable polymer (e.g., PGA or PLLA). The sheath may be impregnated with pharmaceutical substances such as anti-thrombogenics, anti-inflammatory agents, anti-proliferative agents, anti-platelet agents, etc. Narrow tubular hinges 22a, 22b having openings 24a, 24b are formed on opposite edges of the sheet as shown in FIGS. 3A and 3B.

When assembled for implantation, the anchor 10 is compressed into the recessed portion 16 (FIG. 1A) on the implant 12. The sheath 20 is wrapped around the compressed anchor and into the tubular shape shown in FIG. 3C, and the hinges 22b are interleaved with hinges 22a. A wire 26 (FIG. 2A) is passed through the openings 24a, 24b (FIGS. 3A and 3B) to retain the sheath in the tubular position and to keep it in place on the anchor 10. Wire 26 includes a distal stop 28 that is sufficiently small to pass through all of the openings 24a, 24b except the most proximal one of the openings, and thus creates a permanent tether between the sheath 20 and the wire 26. A proximal stop 30 on the wire is too large to pass through the openings 24a, 24b and thus prevents the wire from sliding forward independently of the sheath 20.

Implantation of the medical implant 12 using the anchor 10 and sheath 20 will next be described. First, the medical implant 12 with the anchor 10 and sheath 20 packaged as shown in FIG. 2A are inserted into the vasculature using appropriate techniques. For example, the medical implant with the anchor and sheath thereon may be advanced over a guidewire passed into the femoral vein to the inferior vena cava or superior vena cava, or into the subclavian. The proximal-most end of wire 26 should remain outside the body at all times.

Figure 4A:
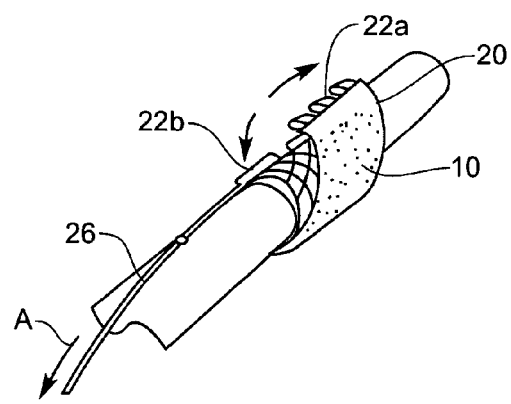
FIGS. 4A through 4C are perspective views similar to FIG. 2, showing a series of steps for deploying the retention device and removing the sheath.
Figure 4B:
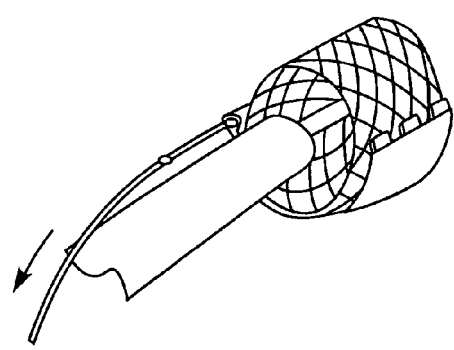
Figure 4C:
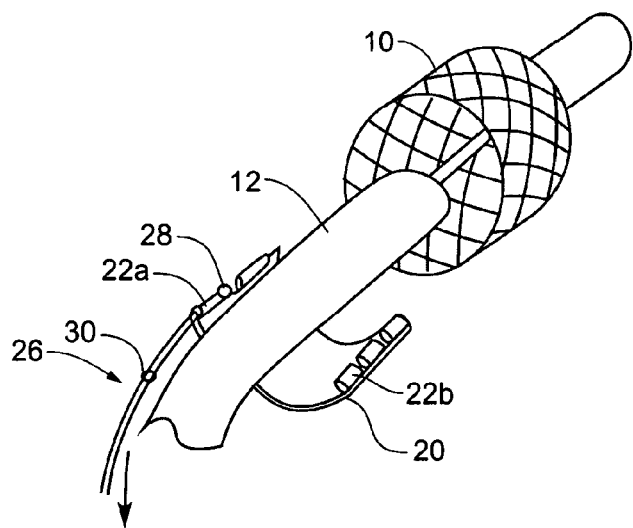

Once the medical implant 12 has been advanced to the desired implant location within the vein (or artery), the wire 26 is pulled from outside the body as indicated by arrow A in FIG. 4A, causing distal stop 28 to pass through the hinges 22a, 22b. Removal of the wire allows the sheath 20 to open in a clamshell fashion in response to the radial expansion forces of the anchor 10. Because the distal stop 28 cannot pass through the most proximal one of the openings in hinges 22a, 22b, the sheath 20 is withdrawn from the body by continued pulling on the wire as shown in FIG. 4C. The anchor expands into contact with the surrounding vessel wall, thereby retaining the implant within the vessel. If a biodegradable sheath is used in place of the sheath 20, it may be left behind within the vessel, in a position between the anchor 10 and the adjacent wall (see the position of sheath 20 in FIG. 4B) until such time as it degrades.

In an alternative sheath configuration shown in FIGS. 5A and 5B, the sheath 21 is a ribbon of sheath material wound around the compressed device 10. In this case, the wire 26 is attached to a distal end of the ribbon sheath 21. Retracting the wire 26 as shown in FIG. 5B unwraps the ribbon from the anchor 10 and thereby allows the anchor 10 to be released into its expanded position. As another example, the sheath may include perforations that allow the sheath to tear away from the anchor when the wired is pulled. As still another alternative, the sheath may be an elongate tube that is telescopically received over the implant and anchor. The tube may be sufficiently long to extend outside the body, such that it may be withdrawn in a proximal direction to release the anchor into its expanded position and then completely withdrawn from the vessel.

An elongate tubular liner (not shown) having a length that preferably exceeds the length of the implant may be deployed within the vessel prior to implantation of the implant 12 and anchor 10. The polymeric liner helps to reduce the risk of trauma to the vessel tissue during explantation of the implant and anchor.

During implantation, the liner is deployed in the desired anatomic location before the implant is moved into place. Once the liner is in place, the implant and anchor are deployed as described above. Over time the liner may become endothelialized, particularly at its edges. However, the endothelial growth is self-limiting to the edge or rim of the liner due to increasing distance from a sustaining blood supply and should not reach the anchor 10. Thus, when it is necessary to explant the implant 12 permanently or for servicing (such as to replace a battery for example) the anchor may be grabbed by a surgical instrument with the outer liner acting as a protective layer for the vessel. The liner may be left in place following removal of the anchor 10 and implant 12. If the implant 12 (or a replacement) is to be later re-implanted, it may be returned to its original location within the liner.

Alternative Anchor Configurations

As discussed, the anchor may be configured in various ways without departing from the scope of the present invention. For example, referring to FIGS. 6A through 6C, anchor 32 may be formed of a sheet of material such as 31 6L stainless steel, spring steel, or nitinol. As shown in FIG. 6B, a retaining member 34 which engages the medical implant (such as in a manner similar to that shown in connection with the FIG. 1A embodiment) is formed at one edge of the sheet, such as by rolling the edge into a tube and then permanently or detachably securing the tube to the medical implant by welding, adhesives, snap-fit, crimping, or other means. The sheet is rolled into a narrow tube as shown in FIG. 6B for passage through the blood vessels during implantation, and is then allowed to open to its deployed position shown in FIG. 6C once at the desired implant location to anchor the medical implant within the vessel. As with the FIG. 1A anchor 10, a removable sheath such as the sheath 20 of FIG. 2A may be used to retain the anchor in a collapsed position during implantation.

Figure 7:
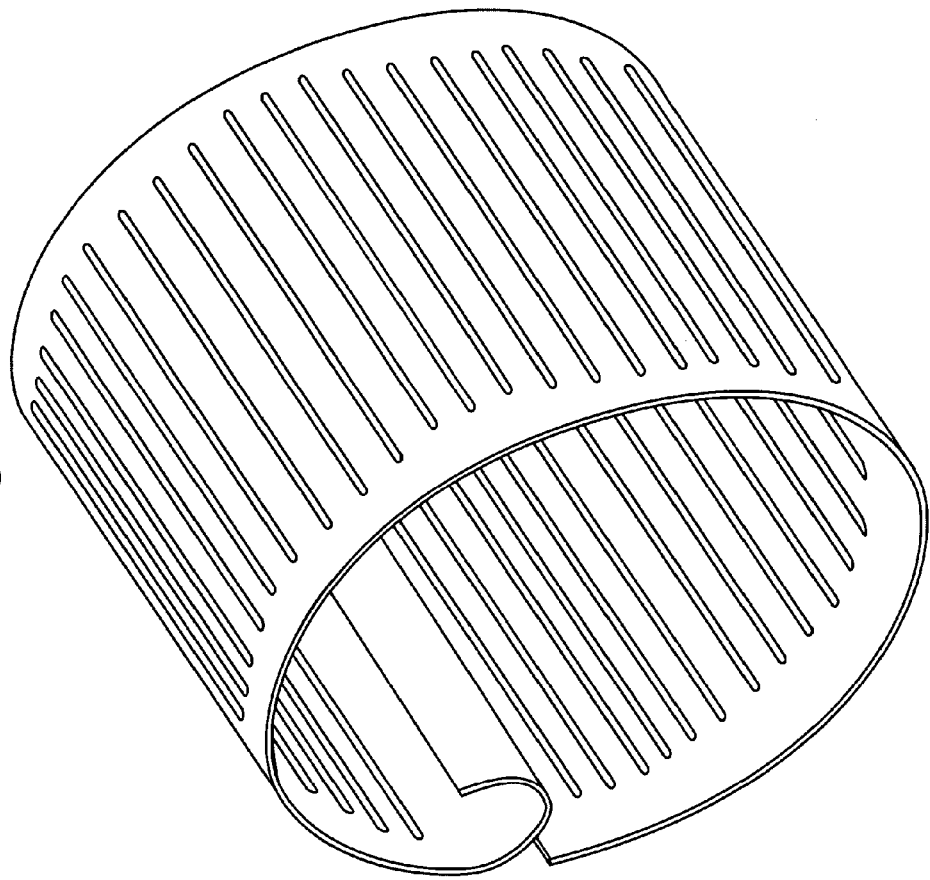
FIG. 7 is a perspective view of a retention device similar to the retention device of FIGS. 6A-6C.

As shown in FIG. 7, the sheet of the FIG. 6A embodiment may include fenestrations 40 of any geometry to provide flexibility to the sheet material and to promote tissue integration, if desired.

As yet another example shown in FIGS. 8A through 8D, an anchor 36 may be formed of a wire (e.g., stainless steel or nitinol) wound into a helical coil. If ribbon is used to form the anchor 36, fenestrations such as those shown in FIG. 7 may be formed in the ribbon surface. Retaining members, which may be rings 38a, 38b, may be formed by shaping the ends of the wire or ribbon into loops or cuffs and by securing the rings to the medical implant 12 as shown in FIG. 8D. For deployment, the coil is compressed around the medical implant 12 as shown in FIG. 8B, and is then released from the compressed state once the medical implant 12 has been placed in the desired implant location. Again, a removable sheath may be used to retain the anchor in the collapsed position and removed to allow the anchor to spring to the expanded position.

Figure 9:
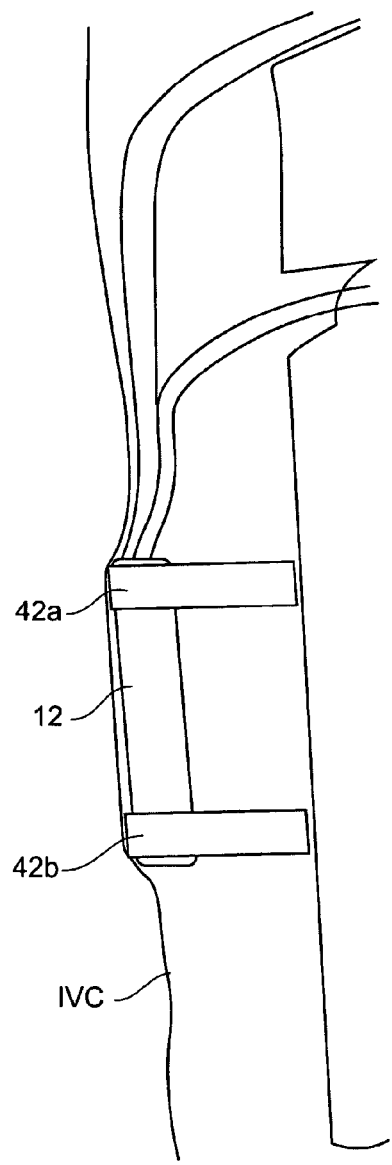
FIG. 9 is a side elevation view of an alternative embodiment using anchoring rings to anchor a medical implant within a blood vessel.

In FIG. 9, another alternative anchor configuration is shown positioned within a blood vessel. This configuration uses one or more anchoring bands made of stainless steel, nitinol, shape memory polymer or similar material. FIG. 9 shows two such bands 42a, 42b at proximal and distal positions on the medical implant 12, although it should be appreciated that the number and position of the bands may vary. Each band is attached to the medical implant 12 using techniques described above (e.g., using a barrier membrane, an attachable cuff, welding, adhesives etc.) or other methods. As shown, in this and the other embodiments the force of the anchor against the vessel walls may cause the vessel to distend outwardly due to the vessel's compliance. Because the implant 12 occupies the distension in the vessel, the presence of the implant causes minimal (if any) obstruction to blood flowing through the vessel.

FIG. 10A-10D show yet another anchor configuration in which each anchor 44 includes preferably one or two stainless steel or nitinol wires or ribbons 45a, 45b formed or cut into an alternating geometric pattern. If two or more such wires/ribbons 45a, 45b are used as shown, longitudinal struts 43 may extend between the wires/ribbons to enhance structural rigidity.

Figure 10A:
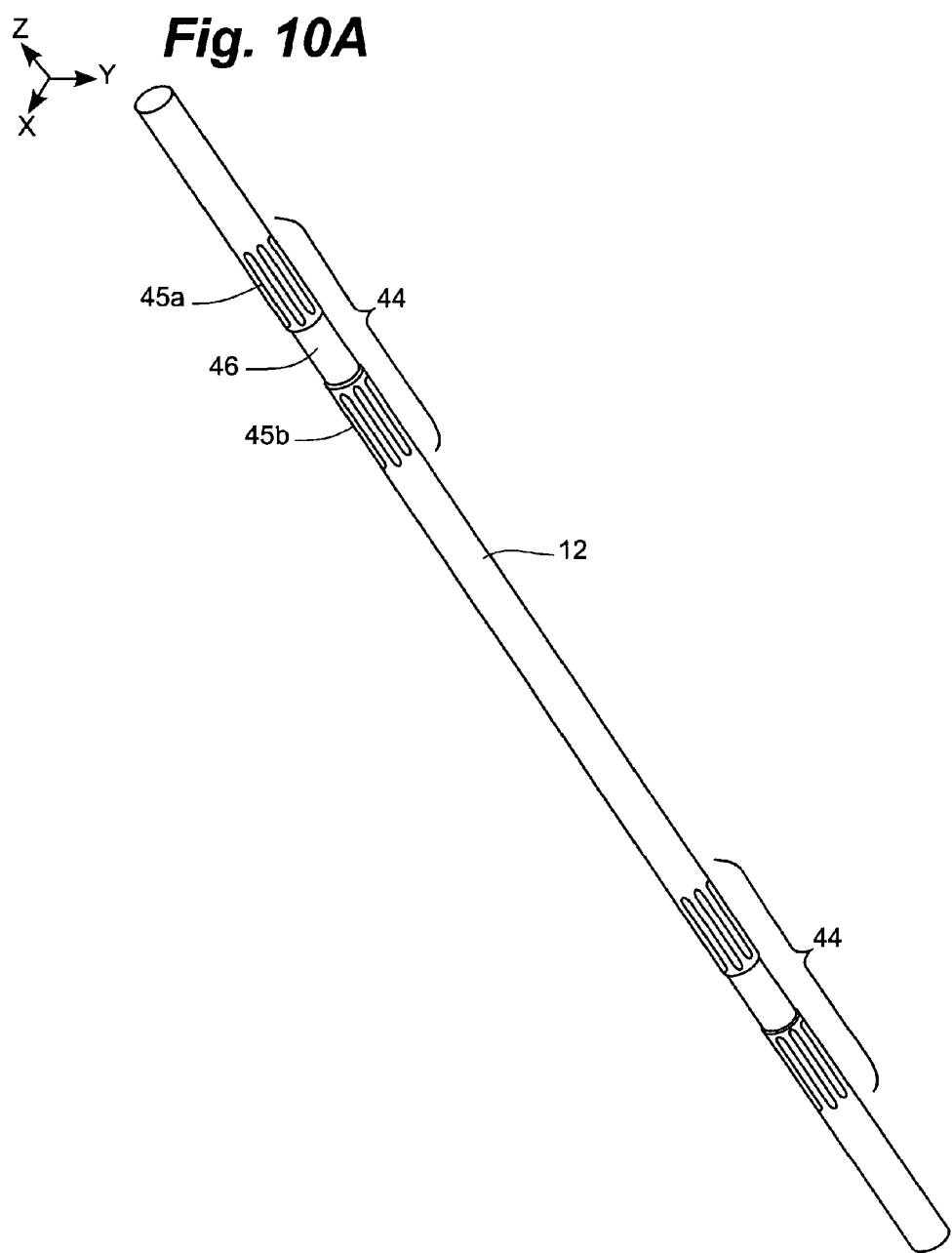
FIG. 10A shows two units of an alternative embodiment of a retention device attached to a medical implant. The retention device is shown in the retracted position.

Two anchors 44 are shown in the FIG. 10A embodiment, although naturally one, two or more such anchors may alternatively be used as is also the case with the other embodiments. Each anchor 44 is attached to the medical implant 12 by a collar 46, although other connections may also be used. The medical implant 12 may include a recessed portion 47, in which case collar 46 may be connected to the recessed portion 47 preferably using a snap fit (or any of the methods described previously) to allow the anchor 44 and the implant 12 to be separated if desired.

Figure 10B:
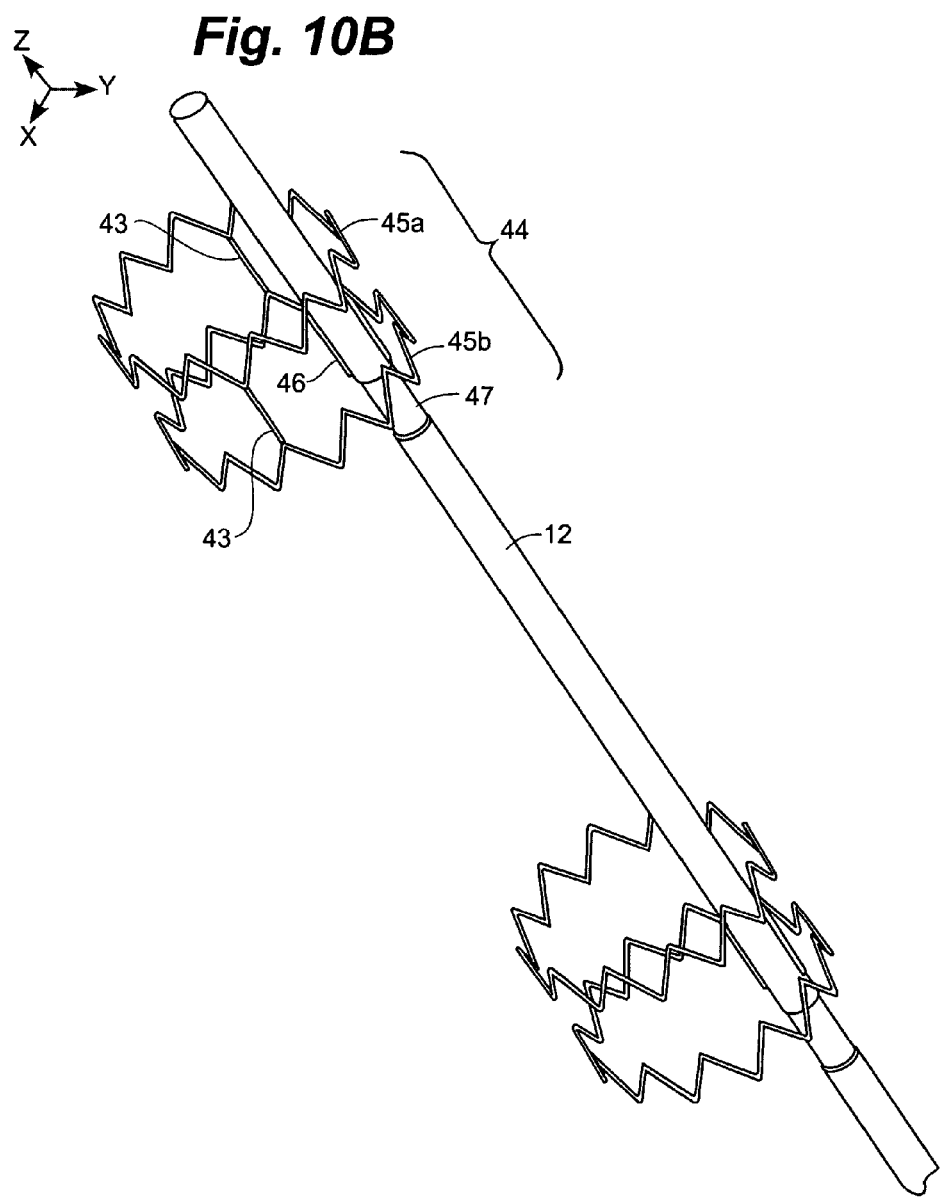
FIG. 10B is a side elevation view showing the retention devices of FIG. 10A in the expanded position.
Figure 10E:
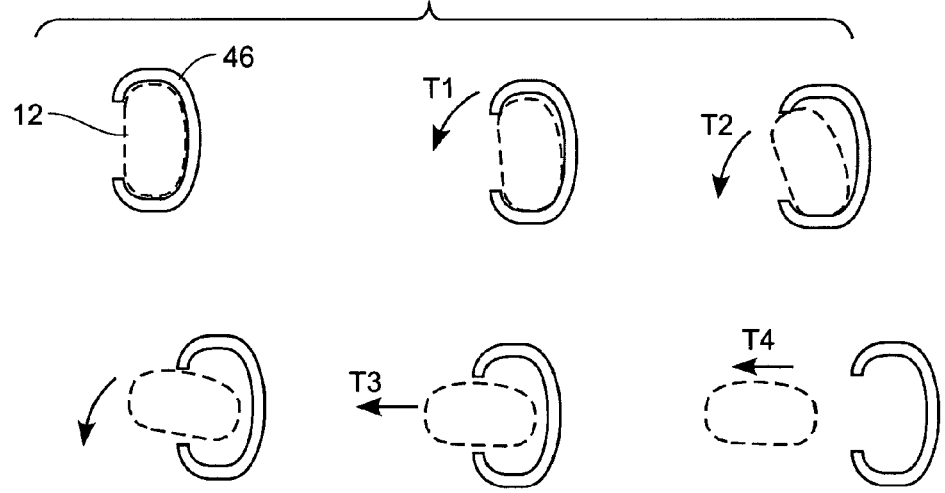
FIG. 10E is a sequence of top plan views of the collar of the retention device of FIG. 10C, illustrating removal of the medical implant from the collar.

The anchor 44 is expandable from the position shown in FIG. 10A to the position shown in FIGS. 10B-10D in which it contacts the surrounding walls of the vessel, thereby holding the medical implant in the desired location. The recessed portion 47 may have a sufficiently long longitudinal dimension to allow the wires/ribbons 45a, 45b to seat within it when the anchor 44 is in the un-expanded position, so as to facilitate streamlined movement of the anchor and medical implant through the vessel.

Figure 10F:
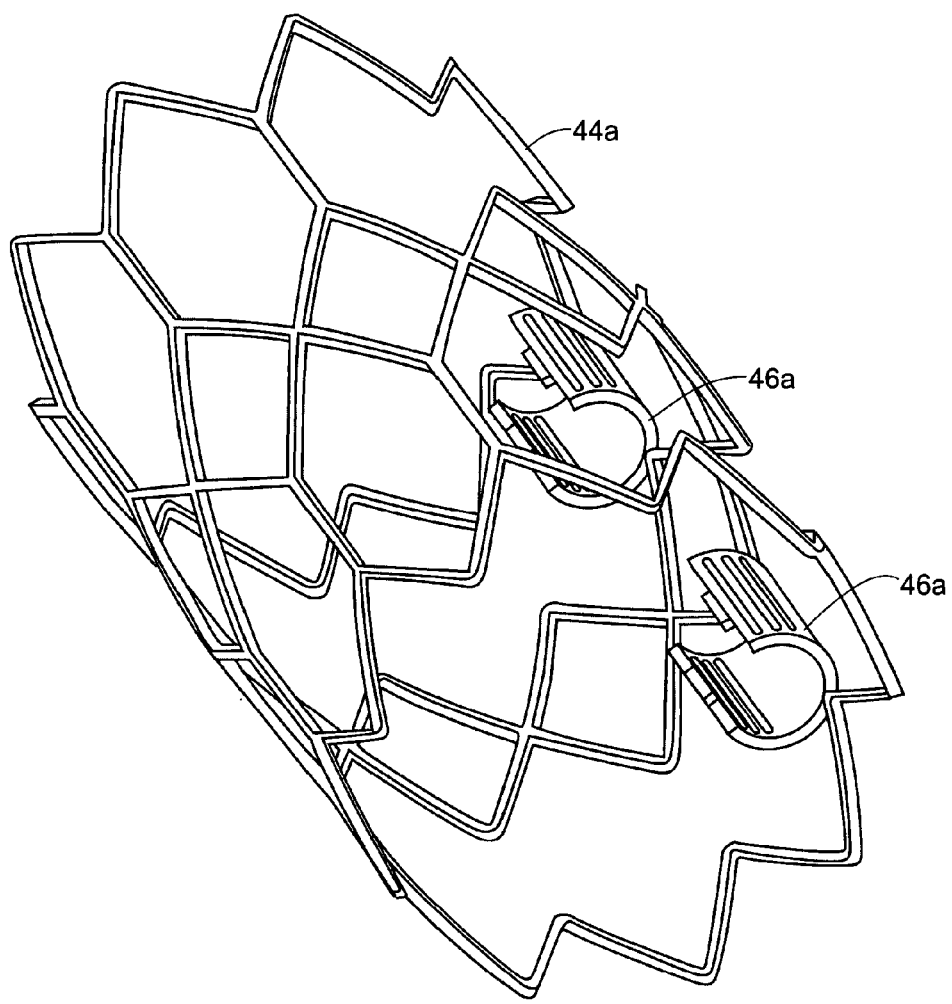
FIG. 10F is a variation of the retention device of FIG. 10B.

As shown in FIG. 10D, both the collar 48 and the recessed portion 47 of the implant may include an elliptical cross-section. If it becomes necessary to remove the medical implant from the patient's body, the medical implant may be torqued as indicated by arrows T1 and T2 in FIG. 10E, causing the body of the implant to cam the edges of the collar 48 to a slightly opened position, thereby allowing the implant to be passed between the edges as indicated by arrows T3 and T4. FIG. 10F shows an anchor 44a that is a modified version of the FIG. 10B anchor. As with the FIG. 10B anchor, collars 46a may be permanently or removably attached to the implant.

FIGS. 11A-11C show an anchor 48 that is similar to those of FIG. 8, but that differs in that collar 50 for attachment to the medical implant 12 is positioned co-axially with the anchor 48. Support struts 52 connect the collar and the anchor 48. A polymeric and/or elastomeric (e.g., polyurethane or silicone or similar materials known in the art) membrane seal may stretch across the opening in the collar 50 and have an opening for receiving the medical implant 12 so as to stabilize the medical implant within the collar. This membrane may include a lubricious coating on at least its proximal side to facilitate passage of the medical implant through its opening. The anchor 48 may take the form of a ring or baud as shown, or it may have another configuration such as that shown in the FIG. 10B or 10F embodiments. As shown in FIG. 11D, an alternative anchor 48a is similar to that anchor 48 of FIG. 11A, but has an asymmetrical shape including a laterally protruding section 49. Collar 50a and struts 52a are disposed within the protruding section 49. When implanted, the protruding section 49 creates a bulge in the vessel similar to that shown in FIG. 8, thereby maintaining proper blood flow through the vessel, while simultaneously keeping the medical implant out of direct contact with the vessel wall and thereby lessening the chance for growth of tissue onto the implant. Direct contact between the implant and vessel wall could lead to slight injury of the tissue which could in turn trigger cellular proliferation and result in encapsulation of the device with fibrotic, muscle and connective tissue.

Figure 12A:
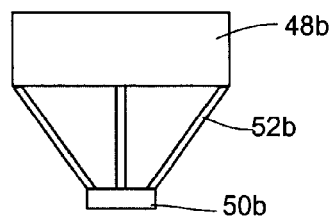
FIG. 12A is a side elevation view of yet another embodiment of a retention device.
Figure 12B:
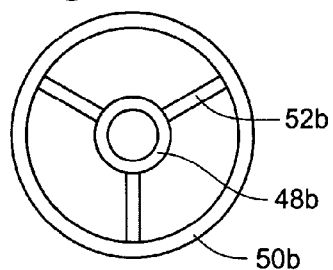
FIG. 12B is a top plan view of the retention device of FIG. 12A.
Figure 12C:
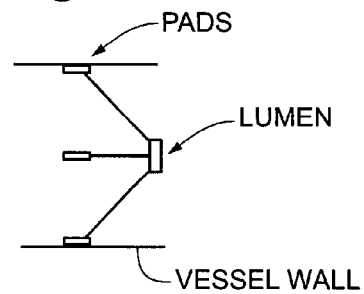
FIG. 12C is a cross-sectional side view showing the retention device of FIG. 12A within a vessel.

FIGS. 12A-12C show an embodiment that is similar to the embodiment of FIGS. 11A-11C, but that differs in that the anchor 48*b* and cuff 50*b* are longitudinally offset from one another. Struts 52*b* extend angularly between anchor 48*b* and cuff 50*b*.

In another embodiment shown in FIGS. 13A and 13B, a pair of cuffs 54 are connected by elongate strut members 56. In this embodiment, the cuffs 54 engage the medical implant, and retention within the vessel is provided by the strut members 56 themselves. The strut members are moveable between a compressed/retracted position (not shown) and the expanded position shown in FIGS. 13A and 13B in which the strut members bow outwardly into contact with the vessel wall, causing the longitudinal dimension of the device to shorten.

Various embodiments of retention devices have been described herein. These embodiments are given by way of example and are not intended to limit the scope of the present invention. It should be appreciated, moreover, that the various features of the embodiments that have been described might be combined in various ways to produce numerous additional embodiments. Moreover, while various materials, dimensions, shapes; implantation locations, etc. have been described for use with disclosed embodiments, others besides those disclosed may be utilized without exceeding the scope of the invention.

All prior patents and applications referred to herein, including for purposes of priority, are incorporated herein by reference.

The invention claimed is:

1. A method for retaining a medical device within a blood vessel, comprising:
   providing an elongate intravascular medical device including a retention device;
   with the retention device in a compressed position, positioning the retention device and the medical device in the blood vessel, wherein the elongate intravascular medical device comprises an elongate pulse generator having a generally cylindrical construction with a circular cross-section that forms a hermetically sealed housing containing circuitry and a power supply, the elongate pulse generator being configured to be flexible about a longitudinal axis such that positioning the medical device includes bending of the pulse generator in response to passage of the device through curved regions of the blood vessel; and
   expanding the retention device to an expanded position to retain the medical device within the blood vessel such that the medical device is positioned generally coaxially within the blood vessel.

2. A system, comprising:
   an elongate intravascular medical device comprising an elongate pulse generator having a generally cylindrical construction with a circular cross-section that forms a hermetically sealed housing containing circuitry and a power supply, the elongate pulse generator being configured to be flexible about a longitudinal axis such that the medical device bends in response to passage of the pulse generator through curved regions of the blood vessel; and
   means for retaining the medical device within a blood vessel of a patient such that the medical device is positioned generally coaxially within the blood vessel.

3. A method for providing a medical device and providing instructions for retaining the medical device within a blood vessel of a patient, comprising:
   providing a retention device expandable from a compressed position to an expanded position;
   providing an elongate intravascular medical device, wherein the elongate intravascular medical device comprises an elongate pulse generator having a generally cylindrical construction with a circular cross-section that forms a hermetically sealed housing containing circuitry and a power supply; and
   providing instructions to implant the medical device in the blood vessel of the patient, including:
      positioning the medical device in the blood vessel with the retention device positioned on the medical device in the compressed position; and
      expanding the retention device to the expanded position to retain the medical device within the blood vessel such that the medical device is positioned generally coaxially with the blood vessel
   wherein the elongate pulse generator is configured to be flexible about a longitudinal axis such that the step of positioning the medical device includes bending of the pulse generator in response to passage of the device through curved regions of the blood vessel.

* * * * *